(12) United States Patent
Bittar et al.

(10) Patent No.: US 10,143,214 B2
(45) Date of Patent: *Dec. 4, 2018

(54) METHOD AND DEVICE FOR BREWING A BEVERAGE

(71) Applicant: Conopco, Inc., Englewood Cliffs, NJ (US)

(72) Inventors: Ahmad Bittar, Cambridge (GB); David Murray Cross, Letchworth (GB); Michael Paton, Royston (GB); Alistair David Smith, Bangkok (TH); Daniel Thomas Toon, Epping (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/408,634

(22) PCT Filed: Jul. 2, 2013

(86) PCT No.: PCT/EP2013/063946
§ 371 (c)(1),
(2) Date: Dec. 17, 2014

(87) PCT Pub. No.: WO2014/006050
PCT Pub. Date: Jan. 9, 2014

(65) Prior Publication Data
US 2015/0297018 A1 Oct. 22, 2015

(30) Foreign Application Priority Data

Jul. 6, 2012 (EP) ..................................... 12175405
Jul. 6, 2012 (EP) ..................................... 12175406
(Continued)

(51) Int. Cl.
*A23F 3/18* (2006.01)
*B65D 85/804* (2006.01)
(Continued)

(52) U.S. Cl.
CPC ................ *A23F 3/18* (2013.01); *A23F 5/262* (2013.01); *A23L 2/52* (2013.01); *A47J 31/06* (2013.01);
(Continued)

(58) Field of Classification Search
CPC ............ B65D 85/8043; B65D 85/8046; B65D 85/804; A47J 31/46; A47J 31/407;
(Continued)

(56) References Cited

U.S. PATENT DOCUMENTS 3,975,996 A 8/1976 Vitous
4,136,202 A 1/1979 Favre
(Continued)

FOREIGN PATENT DOCUMENTS

AT 511357 11/2007
AT 511332 11/2012
(Continued)

OTHER PUBLICATIONS

Harney, Michael, The Harney & Sons Guide to Tea, Penguin Press, 2008, p. 12.*
(Continued)

*Primary Examiner* — Hong Thi Yoo
(74) *Attorney, Agent, or Firm* — Foley & Lardner LLP

(57) ABSTRACT

A method of preparing a tea beverage in a capsule-based brewing device is provided, the device comprising an infusion chamber (10); a capsule holder (20) sized and shaped so as to receive a capsule (30); a filter (25); an openable and closable passage (29) which terminates in an orifice (40); a vessel (60) located beneath the orifice (40) and having a spout (63); the method comprising the steps of: introducing liquid and infusible beverage material from the capsule (30) into the infusion chamber (10) so as to brew the beverage; and then after brewing has taken place for a sufficient time,
(Continued)

opening the passage (29) to allow the beverage to flow from the infusion chamber (10) through the filter (25), along the passage (29), through the orifice (40), into the vessel (60) and out from the spout (63).

4 Claims, 3 Drawing Sheets

(30) Foreign Application Priority Data

| Mar. 21, 2013 | (EP) | .................................... 13160324 |
|---|---|---|
| Mar. 21, 2013 | (EP) | .................................... 13160325 |
| Mar. 21, 2013 | (EP) | .................................... 13160326 |
| Mar. 21, 2013 | (EP) | .................................... 13160328 |
| Mar. 21, 2013 | (EP) | .................................... 13160342 |

(51) Int. Cl.
    *A47J 31/44*     (2006.01)
    *A47J 31/06*     (2006.01)
    *G01N 27/02*     (2006.01)
    *A47J 31/40*     (2006.01)
    *A23F 5/26*     (2006.01)
    *A23L 2/52*     (2006.01)
    *A47J 31/46*     (2006.01)

(52) U.S. Cl.
    CPC ........ *A47J 31/0605* (2013.01); *A47J 31/0615* (2013.01); *A47J 31/0642* (2013.01); *A47J 31/407* (2013.01); *A47J 31/44* (2013.01); *A47J 31/4492* (2013.01); *A47J 31/46* (2013.01); *B65D 85/804* (2013.01); *B65D 85/8043* (2013.01); *G01N 27/025* (2013.01); *A23V 2002/00* (2013.01); *B65D 2203/00* (2013.01); *Y02W 30/807* (2015.05)

(58) Field of Classification Search
    CPC .... A47J 31/0668; A47J 31/06; A47J 31/3623; A47J 31/3676; A47J 31/369; A47J 31/14; A47J 31/405; A47J 31/368; A47J 31/3695; A47J 31/0605; A47J 31/10; A47J 31/18; A47J 31/0642; A23F 3/18
    USPC .............. 99/295, 302 R, 289, 283, 279, 323; 426/433, 431, 77, 435, 115, 425
    See application file for complete search history.

(56) References Cited

U.S. PATENT DOCUMENTS

| 4,253,385 | A | * | 3/1981 | Illy .................... A47J 31/3685 |
|---|---|---|---|---|
| | | | | 99/281 |
| D311,138 | S | | 10/1990 | Chanel |
| 4,983,410 | A | | 1/1991 | Dinos |
| D322,539 | S | | 12/1991 | Under |
| 5,325,765 | A | | 7/1994 | Sylvan et al. |
| 5,425,480 | A | | 6/1995 | Rabenau et al. |
| 5,619,904 | A | | 4/1997 | Di Nunzio |
| 5,813,317 | A | | 9/1998 | Chang |
| D407,640 | S | | 4/1999 | Nelson et al. |
| 5,947,004 | A | | 9/1999 | Huang |
| 6,009,792 | A | | 1/2000 | Kraan |
| D420,856 | S | | 2/2000 | Yeo et al. |
| D425,416 | S | | 5/2000 | Denham et al. |
| 6,142,063 | A | | 11/2000 | Beaulieu et al. |
| D436,532 | S | | 1/2001 | Richardson |
| D438,103 | S | | 2/2001 | Edwards et al. |
| D445,674 | S | | 7/2001 | Pritchett |
| D445,675 | S | | 7/2001 | Richardson |
| 6,316,753 | B2 | | 11/2001 | Clothier et al. |
| 6,382,083 | B2 | | 5/2002 | Schmed |
| D462,900 | S | | 9/2002 | Yamada et al. |
| D477,186 | S | | 7/2003 | de Groote et al. |
| D495,189 | S | | 8/2004 | Cahen |
| 6,786,134 | B2 | | 9/2004 | Green |
| D506,926 | S | | 7/2005 | Halliday et al. |
| D520,185 | S | | 5/2006 | Zeng et al. |
| D539,643 | S | | 4/2007 | Abel |
| D540,608 | S | | 4/2007 | Cahen |
| D549,361 | S | | 8/2007 | To et al. |
| D571,656 | S | | 6/2008 | Maslowski |
| 7,540,232 | B2 | | 6/2009 | Bates et al. |
| D602,303 | S | | 10/2009 | Cahen |
| D606,363 | S | | 12/2009 | Aardenburg |
| 7,640,843 | B2 | | 1/2010 | Halliday et al. |
| D616,251 | S | | 5/2010 | Heiberg et al. |
| D624,785 | S | | 10/2010 | Rousselin |
| 7,854,192 | B2 | | 12/2010 | Denisart et al. |
| D630,880 | S | | 1/2011 | Zimmermann |
| D632,568 | S | | 2/2011 | Caldwell et al. |
| D643,682 | S | | 8/2011 | Asthon |
| 8,010,050 | B2 | | 8/2011 | Kennedy |
| D649,392 | S | | 11/2011 | Cahen |
| D652,718 | S | | 1/2012 | Caldwell et al. |
| D659,022 | S | | 5/2012 | Kemner |
| D666,451 | S | | 9/2012 | Cheng |
| D670,539 | S | | 11/2012 | Starr et al. |
| D672,188 | S | | 12/2012 | Luippold et al. |
| 8,333,144 | B2 | | 12/2012 | Boussemart |
| D681,386 | S | | 5/2013 | Pininfarina |
| D684,043 | S | | 6/2013 | Brown et al. |
| D688,392 | S | | 8/2013 | Tsai |
| D689,768 | S | | 9/2013 | Inderbitzin |
| D694,620 | S | | 12/2013 | Hansen |
| D697,399 | S | | 1/2014 | Parmar et al. |
| 8,690,013 | B2 | | 4/2014 | Kneer |
| D704,494 | S | | 5/2014 | Blanc |
| 8,770,095 | B2 | | 7/2014 | Pecci et al. |
| 8,820,974 | B2 | | 9/2014 | Chang |
| D715,465 | S | | 10/2014 | Hasuo et al. |
| 8,871,285 | B2 | | 10/2014 | Markoulis et al. |
| 8,993,018 | B2 | | 3/2015 | Bucher et al. |
| D732,386 | S | | 6/2015 | Paton et al. |
| 9,603,201 | B2 | | 3/2017 | Bogel et al. |
| 9,625,280 | B2 | | 4/2017 | Frese |
| 2002/0048621 | A1 | | 4/2002 | Boyd et al. |
| 2002/0078831 | A1 | | 6/2002 | Cai |
| 2002/0148357 | A1 | | 10/2002 | Lazaris et al. |
| 2003/0033938 | A1 | | 2/2003 | Halliday et al. |
| 2005/0015348 | A1 | | 1/2005 | Knepler |
| 2005/0172822 | A1 | | 8/2005 | Macchi et al. |
| 2005/0236323 | A1 | | 10/2005 | Oliver et al. |
| 2006/0065127 | A1 | | 3/2006 | Dalton et al. |
| 2006/0174770 | A1 | | 8/2006 | Jordana |
| 2008/0072766 | A1 | * | 3/2008 | Kobylarz ............ A47J 31/0576 |
| | | | | 99/279 |
| 2008/0105130 | A1 | | 5/2008 | Koeling et al. |
| 2008/0148948 | A1 | | 6/2008 | Evers et al. |
| 2009/0155422 | A1 | | 6/2009 | Ozanne |
| 2009/0220650 | A1 | | 9/2009 | Ozanne |
| 2010/0055252 | A1 | | 3/2010 | Marina et al. |
| 2010/0132564 | A1 | | 6/2010 | Ozanne et al. |
| 2010/0154644 | A1 | | 6/2010 | Skalski et al. |
| 2010/0173056 | A1 | | 7/2010 | Yoakim et al. |
| 2010/0180775 | A1 | | 7/2010 | Kollep et al. |
| 2010/0239734 | A1 | | 9/2010 | Yoakim et al. |
| 2010/0263546 | A1 | | 10/2010 | Leuzinger et al. |
| 2010/0288131 | A1 | | 11/2010 | Kilber et al. |
| 2011/0052761 | A1 | | 3/2011 | Yoakim et al. |
| 2011/0303095 | A1 | | 12/2011 | Fu et al. |
| 2011/0308399 | A1 | | 12/2011 | Jung |
| 2012/0070543 | A1 | | 3/2012 | Mahlich |
| 2012/0098526 | A1 | | 4/2012 | Bucher et al. |
| 2013/0095212 | A1 | | 4/2013 | Beer |
| 2013/0119930 | A1 | | 5/2013 | Sakoda et al. |
| 2013/0129872 | A1 | | 5/2013 | Kruger |
| 2013/0302476 | A1 | | 11/2013 | Abegglen et al. |
| 2014/0196608 | A1 | | 7/2014 | Amrein et al. |
| 2014/0272016 | A1 | | 9/2014 | Nowak |
| 2014/0356484 | A1 | | 12/2014 | Capitani |
| 2015/0143999 | A1 | | 5/2015 | Cross et al. |

(56) References Cited

U.S. PATENT DOCUMENTS

| | | |
|---|---|---|
| 2015/0173558 A1 | 6/2015 | Cross et al. |
| 2015/0190010 A1 | 7/2015 | Cross et al. |
| 2015/0203285 A1 | 7/2015 | Baldo |
| 2015/0239655 A1 | 8/2015 | Schroeder et al. |
| 2016/0045059 A1 | 2/2016 | Cross et al. |
| 2016/0114967 A1 | 4/2016 | Van Belleghem et al. |
| 2016/0270580 A1 | 9/2016 | Smith |
| 2017/0135364 A1 | 5/2017 | Cross et al. |

FOREIGN PATENT DOCUMENTS

| | | |
|---|---|---|
| CA | 289071 | 10/2012 |
| CN | 2636781 | 9/2004 |
| CN | 2636781 | 11/2004 |
| CN | 101056561 | 10/2007 |
| DE | 1772081 | 10/2005 |
| DE | 202012104474 | 1/2013 |
| EA | 0455337 | 3/1991 |
| EA | 1654966 | 10/2004 |
| EP | 0334573 | 9/1989 |
| EP | 0451980 | 3/1991 |
| EP | 0554469 | 8/1993 |
| EP | 1658796 | 5/2006 |
| EP | 1772398 A1 | 10/2006 |
| EP | 1922962 | 11/2006 |
| EP | 1774878 | 4/2007 |
| EP | 1849718 | 10/2007 |
| EP | 1937115 | 7/2008 |
| EP | 2263501 | 12/2010 |
| EP | 2243378 B1 | 6/2011 |
| EP | 2476633 | 7/2012 |
| GB | 1561188 | 2/1980 |
| GB | 2437483 | 4/2006 |
| GB | 2485575 | 5/2013 |
| JP | 5376171 | 7/1978 |
| JP | 54161781 | 11/1979 |
| JP | 57140239 | 9/1982 |
| JP | 10275275 | 10/1998 |
| RU | 2192140 | 11/2002 |
| WO | WO2006038227 | 4/2006 |
| WO | WO2007019993 | 2/2007 |
| WO | WO07042486 | 4/2007 |
| WO | WO2007042415 | 4/2007 |
| WO | WO2007042485 | 4/2007 |
| WO | WO2008025730 | 3/2008 |
| WO | WO2008058576 | 5/2008 |
| WO | WO2008156283 | 12/2008 |
| WO | WO2009130311 | 10/2009 |
| WO | WO2010076263 | 7/2010 |
| WO | WO2011000723 | 1/2011 |
| WO | WO2011000724 | 1/2011 |
| WO | WO2011000725 | 1/2011 |
| WO | WO2011141532 | 11/2011 |
| WO | WO2012010317 | 1/2012 |
| WO | WO2012072508 | 6/2012 |
| WO | WO2013008012 | 1/2013 |
| WO | WO2012144885 | 10/2013 |

OTHER PUBLICATIONS

Containing definition. http://www.dictionary.com/browse/containing, retrieved on Jun. 27, 2017.*
Jan. 1, 2013, Espresso Coffee Club Nespresso Swiss Capsules 2013 p. 1, p. 1.
Oct. 7, 2014, IPRP2 in PCTEP2013063942.
CBTL Caffitaly E Caffe Capsules 2013 p. 1, Jan. 1, 2013, p. 1.
IPRP2 in PCTEP2013063950, Jul. 6, 2014.
Nespresso Single Serve Capsules 2013 p. 1, Jan. 1, 2013, p. 1.
Search Report in EP12175405, dated Jan. 24, 2013.
Search Report in EP12175406, dated Dec. 21, 2012.
Search Report in EP14159168, dated Jun. 24, 2014.
Search Report in PCTEP2013063942, dated Feb. 11, 2014.
Search Report in PCTEP2013063943, dated Feb. 7, 2014.
Search Report in PCTEP2013063946, dated Feb. 6, 2014.
Search Report in PCTEP2013063947, dated Mar. 24, 2014.
Search Report in PCTEP2013063948, dated Mar. 24, 2014.
Search Report in PCTEP2013063949, dated Feb. 6, 2014.
Search Report in PCTEP2013063950, dated Feb. 7, 2014.
Search Report in PCTEP2014054859, dated Jul. 2, 2014.
Written Opinion in EP12175405, dated Jan. 24, 2013.
Written Opinion in EP12175406, dated Dec. 21, 2012.
Written Opinion in PCTEP2013063942, dated Feb. 11, 2014.
Written Opinion in PCTEP2013063943, dated Feb. 7, 2014.
Written Opinion in PCTEP2013063946, dated Feb. 6, 2014.
Written Opinion in PCTEP2013063947, dated Mar. 24, 2014.
Written Opinion in PCTEP2013063948, dated Mar. 24, 2014.
Written Opinion in PCTEP2013063949, dated Feb. 6, 2014.
Written Opinion in PCTEP2013063950, dated Feb. 7, 2014.
Written Opinion in PCTEP2014054859, dated Jul. 2, 2014.
IPRP2 in PCTEP2013063947, dated Nov. 21, 2014.
Copending application for Blanc, U.S. Appl. No. 29/440,100, filed Dec. 9, 2012.
Copending application for Paton et al., U.S. Appl. No. 29/466,849, filed Sep. 12, 2013.
Copending application for Paton et al., U.S. Appl. No. 29/466,853, filed Sep. 12, 2013.
Copending application for Cross et al, U.S. Appl. No. 14/408,617, filed Dec. 17, 2014.
Copending application for Cross et al., U.S. Appl. No. 14/408,623, filed Dec. 17, 2014.
Copending application for Cross et al., U.S. Appl. No. 14/408,624, filed Dec. 17, 2014.
Copending application for Cross et al., U.S. Appl. No. 14/408,635, filed Dec. 17, 2014.
Copending application for Cross et al., U.S. Appl. No. 14/408,639, filed Dec. 17, 2014.
Copending application for Cross et al., U.S. Appl. No. 14/408,638, filed Dec. 17, 2014.
Search Report & Written Opinion in EP15188381, dated Feb. 1, 2016.
Search Report in EP15180266, dated Dec. 9, 2015 (NPL 1).
Written Opinion in EP15180266, dated Dec. 9, 2015 (NPL 2).
Definition of Intersect, Merriam-Webster Dictionary, 2017, 1 Page.
Search Report & Written Opinion in EP17155955, dated May 22, 2017.
Buckley, Joseph; An Introduction to Eddy Current Testing Theory and Technology, 2003. Retrieved from: <https://web.archive.org/web/20030410135725/http://www.joe.buckley.net/papers/eddyc.pdf>.
Measuring and Memory Systems, Kaman Inductive Technology Handbook, 2012, pp. 1-39.
Dyer, Stephen A., In-depth coverage of instrumentation and measurement from the Wiley Encyclopedia of Electrical, Wiley Survey of Instrumentation and Measurement, 2017, pp. 1-5.
Definition for Contain, Dictionary.com, Jun. 27, 2017, pp. 1-4.

* cited by examiner

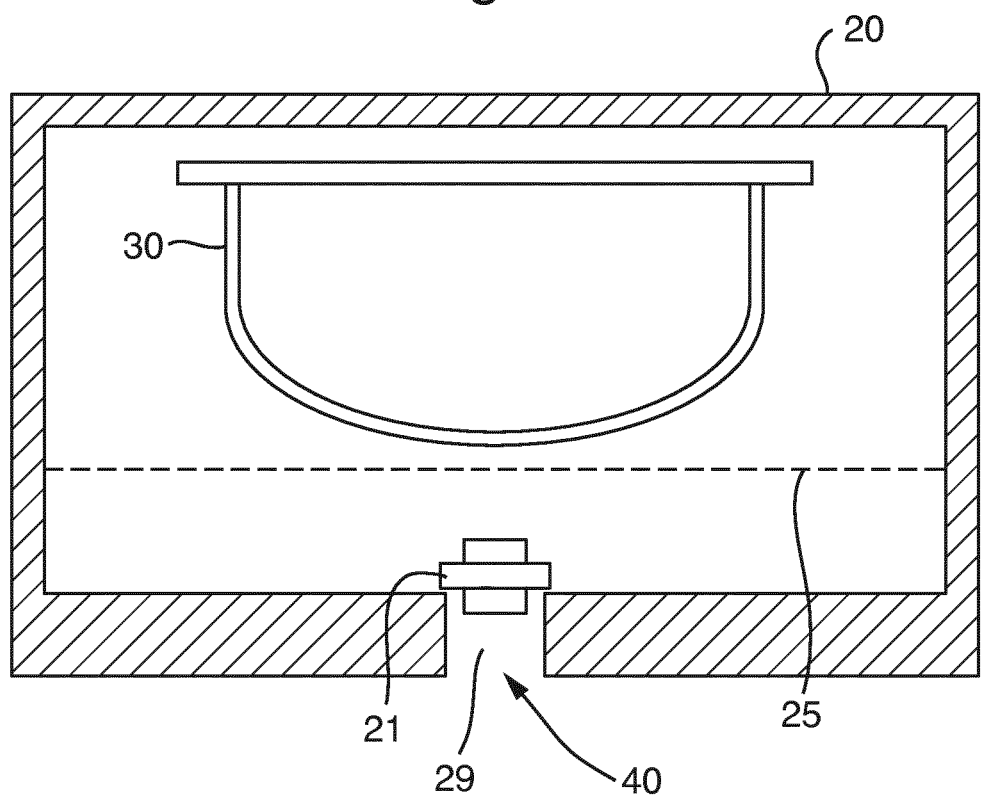

METHOD AND DEVICE FOR BREWING A BEVERAGE

TECHNICAL FIELD OF THE INVENTION

The present invention relates to a method and device for brewing a beverage. In particular, the invention relates to infused beverages such as tea that are brewed in a device having an infusion chamber.

BACKGROUND TO THE INVENTION

Beverages such as tea and coffee are usually prepared in the home using ground coffee, tea bags or loose-leaf tea. However, the long brewing time and mess after brewing are inconvenient.

Devices for automatically brewing tea are known. One type of brewing device, described for example in U.S. Pat. No. 5,619,904 and WO 2008/058576 consists of a brewing container which fits on top of a tea pot. Leaf tea or other beverage material is placed in the brewing container, and hot water is then introduced. Once brewing has been completed, the liquid is transferred from the brewing container into the tea pot. The brewing container is then removed, and the beverage is poured out of the tea pot into a cup. WO 2008/156283 discloses an extractor for extracting loose green tea leaves with pressurized hot water. After extraction, the beverage passes out of the extractor and out through a pipe.

Automatic capsule-based coffee brewing devices are well known. Ground coffee is provided in a single use capsule or cartridge, through which hot water is passed to brew the beverage. The spent coffee material is retained or collected in the capsule after brewing, which makes for easy disposal and no mess. These devices provide a convenient, rapid and consumer-friendly way of brewing beverages. However, whilst these devices are generally recognized by consumers to provide good quality coffee beverages, similar devices for making tea have not always achieved the same acceptance. Consumers often perceive tea from such a brewing device as not being of high quality.

Capsule-based devices for brewing tea have been designed which have a transparent infusion chamber, see for example, WO 2007/042485. The tea leaves immersed in the liquid are visible to the user whilst infusion takes place. After brewing, the tea beverage is dispensed vertically downwards from a spout beneath the infusion chamber. Whilst having a transparent infusion chamber helps to emphasize the quality and "tea-ness" of the beverage, as distinct from coffee making machines, it would nonetheless be desirable to improve the perception of the quality of beverages from devices for making tea. Hence it is an object of the present invention to provide a method for brewing a tea beverage in a capsule-based brewing device which addresses this problem.

BRIEF DESCRIPTION OF THE INVENTION

In a first aspect, the present invention provides a method of preparing a tea beverage in a capsule-based brewing device, the device comprising
 an infusion chamber;
 a capsule holder sized and shaped so as to receive a capsule;
 a filter;
 an openable and closable passage which terminates in an orifice;
 a vessel located beneath the orifice and having a spout;
the method comprising the steps of:
 a) introducing liquid and infusible beverage material from the capsule into the infusion chamber so as to brew the beverage;
 b) after brewing has taken place for a sufficient time, opening the passage to allow the beverage to flow from the infusion chamber through the filter, along the passage, through the orifice, into the vessel and out from the spout.

In a second aspect the present invention provides a capsule-based brewing device, the device comprising
 an infusion chamber;
 a capsule holder sized and shaped so as to receive a capsule;
 a filter;
 an openable and closable passage which terminates in an orifice;
 a vessel located beneath the orifice and having a spout;
 means for introducing liquid and infusible beverage material from the capsule into the infusion chamber so as to brew the beverage;
 a valve for opening the passage to allow the beverage to flow from the infusion chamber through the filter, along the passage, through the orifice, into the vessel and out from the spout.

By dispensing the beverage via the vessel and spout, the beverage pours in an arc, rather than simply being dispensed vertically downwards from the orifice into the cup. This is reminiscent of tea poured from the spout of a tea pot, and emphasizes the quality and "tea-ness" of the beverage.

DETAILED DESCRIPTION OF THE INVENTION

The term "beverage" refers to a substantially aqueous drinkable composition suitable for human consumption. Preferably the beverage comprises at least 85% water by weight of the beverage, more preferably at least 90% and most preferably from 95 to 99.9%.

The term "infusible beverage material" refers to tea plant material, herb plant material, fruit pieces and/or flower material (e.g. petals), which when steeped or soaked in an aqueous liquid release certain soluble substances into the liquid, e.g. flavour and/or aroma molecules. The term 'tea' refers to leaf and/or stem material from *Camellia sinensis* var. *sinensis* or *Camellia sinensis* var. *assamica*. It also includes rooibos obtained from *Aspalathus linearis*. 'Tea' is also intended to include the product of blending two or more of any of these teas. The tea material may be substantially fermented i.e. black tea, semi-fermented i.e. oolong tea, or substantially unfermented i.e. green tea. The term "herb plant material" refers to material which is commonly used as a precursor for herbal infusions. Preferably the herb plant material is selected from chamomile, cinnamon, elderflower, ginger, hibiscus, jasmine, lavender, lemongrass, mint, rosehip, vanilla and verbena. The tea material may additionally comprise fruit pieces (e.g. apple, blackcurrant, mango, peach, pineapple, raspberry, strawberry etc). The tea material can be flavoured and/or spiced, e.g. with bergamot, citrus peel and the like. For the avoidance of doubt, the term "infusible beverage material" does not include coffee material. Preferably the infusible beverage material is dried and has a moisture content of less than 30 wt %, preferably less than 20 wt % and most preferably from 0.1 to 10 wt %. Preferably the infusible beverage material is in the form of particles which have a size (i.e. longest diameter) of from about 2 to about 10 mm, preferably 3 to 7 mm.

The beverage preferably comprises at least 0.01% by weight tea solids. More preferably the beverage comprises from 0.04 to 3%, even more preferably from 0.06 to 2%, most preferably from 0.1 to 1% by weight tea solids.

The term 'brewing' refers to the addition of a liquid, particularly hot water, to an infusible beverage material thereby to form a beverage. Brewing may be carried out at any temperature, but preferably in the range of 80 to 95° C.

The term "infusion chamber" means a vessel which in which infusion of infusible beverage material takes place, and which is large enough both to allow the beverage material to move around in the liquid during infusion, and also to contain a substantial part, at least 50% of the volume of the final beverage. The term "infusion chamber" therefore does not refer to capsules inside which brewing takes place (as is typically the case in coffee machines).

The term "spout" means an element which channels and directs the flow of a liquid, so that the flow of the liquid on leaving the spout has a horizontal component, i.e. it does not flow in a purely vertical downwards direction. Preferably the spout is a projecting tube or gutter.

The term "capsule" includes cartridges, pods, and packages etc., e.g. a rigid or semi-rigid container in which infusible beverage material is or may be packaged. Preferably the capsule comprises a body part and a lid part, the lid part being attached to the body part so as to enclose the infusible beverage material within the capsule. The lid may be made of a thin film, such as foil.

The present invention will now be described with reference to the figures, wherein:

FIG. 3 shows a capsule holder in cross-section

Figure 1:
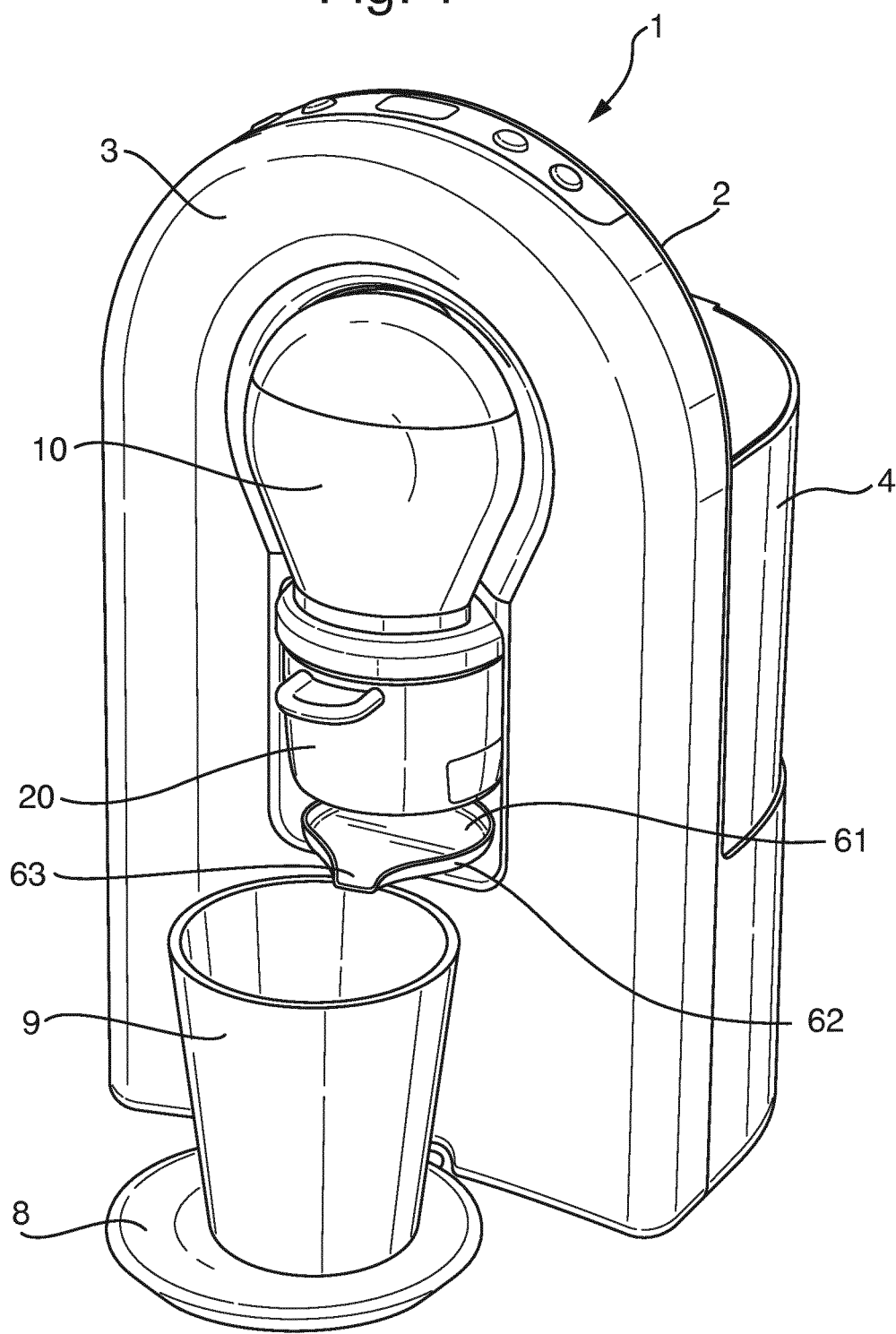
FIG. 1 shows a brewing device according to the invention.

FIG. 1 shows a brewing device according to the invention. The device 1 has a casing 2 with a front side 3 and a rear side 4. An infusion chamber 10 is supported and held in place by a manifold (not shown). A water reservoir, heater, and pump (not shown) are located inside the rear 4 of the casing.

The infusible beverage material is provided in a capsule (not shown). The device has a capsule holder 20 sized and shaped so as to receive the capsule. The capsule holder 20 is shown in position for brewing, wherein the top of the capsule holder is in water-tight contact with the bottom of the infusion chamber 10. In the embodiment shown in FIG. 3, a filter 25 is located in the capsule holder. In an alternative embodiment (not shown) the capsule has a filter in the bottom of the body part. The filter preferably consists of a fine mesh made for example of stainless steel. The mesh size must be sufficiently small to catch small pieces of beverage material but large enough to ensure that draining is not too slow. Preferably, the mesh size is from 100 to 500 microns, more preferably 150 to 300 microns.

Below the capsule holder there is a vessel 60 which has a spout 63. At the bottom of the front side 3 of the casing there is a tray 8 on which a cup is placed when the beverage is dispensed. In the context of the present invention the term "vessel" refers to any object which provides a surface for the beverage to be dispensed onto. In the embodiment shown in FIG. 1, the vessel 60 consists of a flat base 61 having a sidewall 62 around its edge, apart from at the front where there is a spout 63. The vessel could be a cup, a tray, a pipe or any other suitable object. The vessel could be an integral part of the device, for example part of the casing 2, or a separate object (as in the embodiment shown in FIG. 1).

Figure 2:
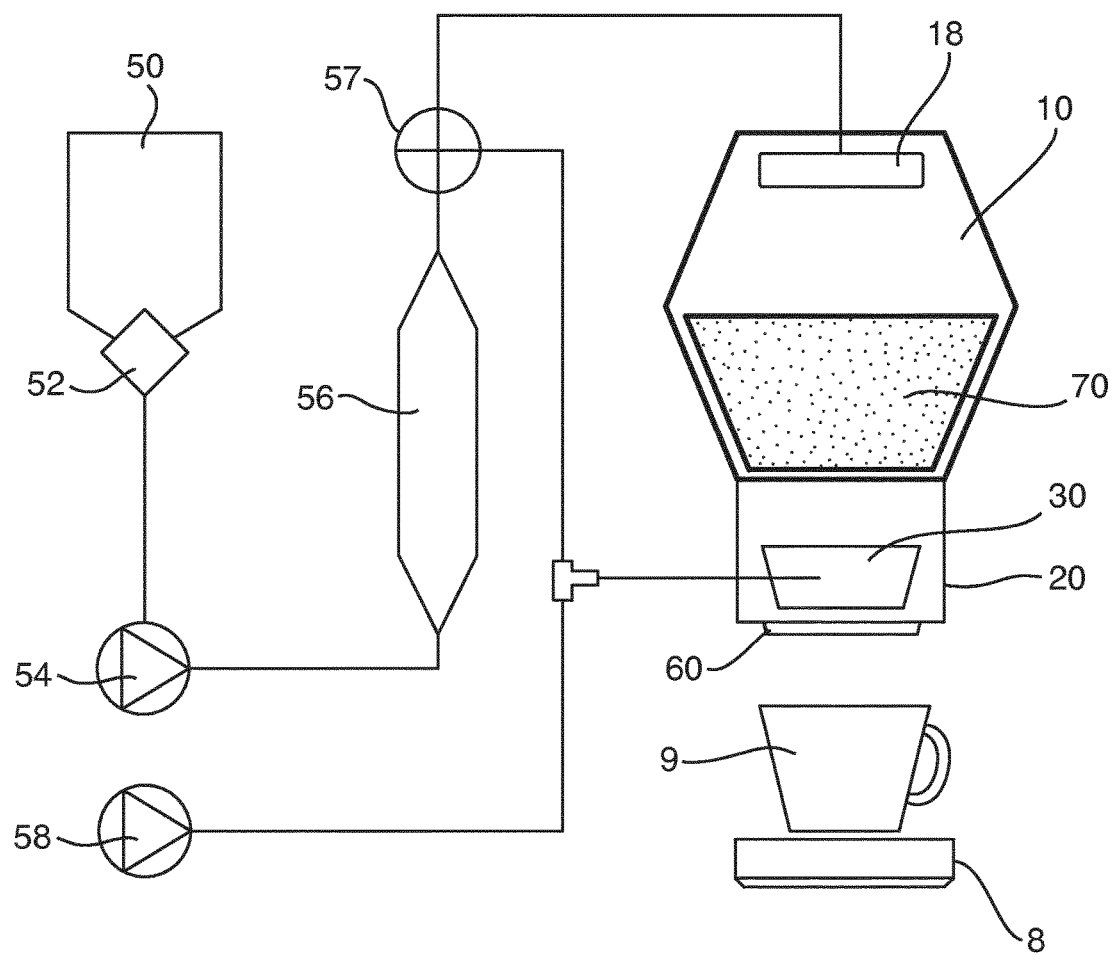
FIG. 2 is a schematic diagram showing the functional main components of the device.

FIG. 2 is a schematic diagram showing the main functional components of the device. Water from the reservoir 50 is fed to the infusion chamber 10 via a water filter 52, a water pump 54, a heater 56 and a valve 57. The capsule holder 20 holds a capsule 30. Beneath the capsule holder 20 there is the vessel 60, and a cup 9 which rests on a tray 8. The valve 57 controls the route the water takes between the heater 56 and the infusion chamber 10. Firstly the water is pumped to the infusion chamber 10 via the capsule, in order to brew a beverage 70. Subsequently, the valve 57 can re-direct the water such that it enters the brewing chamber 10 via a rinse head 18 in order to rinse and/or clean the brewing chamber 10. There is also an air pump 58 which can pump air to the infusion chamber, preferably via the capsule holder.

FIG. 3 shows the capsule holder 20 in cross-section, containing a capsule 30. In the lower part of the capsule holder, there is an openable and closable passage 29 through which the beverage flows during dispensing and which is closed by a drain valve 21 during brewing and which terminates in an orifice 40. In a preferred embodiment, the passage terminates in a plurality of orifices, more preferably from 3 to 7, most preferably 4, 5 or 6 orifices. We have found that having a number of orifices of small diameter results in less dripping at the end of dispensing than a single orifice of a larger diameter.

In use, the device functions as follows. The user places a capsule containing infusible beverage material in the capsule holder. The capsule holder is then placed in communication with the infusion chamber to form a water-tight contact, so that the capsule holder and infusion chamber together form a vessel in which the brewing liquid can be held while brewing takes place. The capsule may have a lid, which needs to be opened or removed in order to release the beverage material. In one embodiment, the lid is removed by the user before the capsule is inserted into the device. Alternatively, the lid is opened automatically by the device after the capsule is inserted into the capsule holder.

The device may have means for recognizing a capsule and/or reading information from a code on the capsule. This allows the capsule to be recognized by the device, so that the device can automatically set the parameters for the brewing operation, such as the brewing time, water temperature etc. It also allows the device to be programmed so that it only operates if the correct type of capsule is present. Thus a valid code signifies that an expected type of capsule is present, and an invalid code signifies an unexpected type of capsule, a capsule that has already been used or that no capsule is present. The recognition system can be of any suitable type, such as mechanical interlocking between the capsule and the capsule holder; optical recognition (e.g. by means of colour, fluorescence or bar code), electrical, magnetic, radio-frequency identification (RFID) chip etc. The device may also have means for allowing the user to adjust the parameters of the brewing operation, such as the brewing time, the cup size etc. The means may suitably consist of buttons or other inputs on the device, together with a control system.

Water is pumped from the reservoir to the heater, which is preferably a flow-though heater. The resulting hot water (and optionally steam) is then pumped to the capsule, for example through a needle. The influx of hot water pushes the infusible beverage material out from the opened capsule into the infusion chamber. The heater and pump are controlled so that the target brew temperature (which is typically in the range 80° C. to 95° C.) is achieved in the infusion chamber. Typically the water flow rate is in the range of 200 to 400 ml/min, and the volume of water is 150 to 300 ml, depending on the desired size of the beverage.

Air may be pumped into the capsule holder or directly into the infusion chamber to create bubbles in the beverage and thereby agitate the beverage material. This not only enhances the visual appearance, but also aids infusion and helps to prevent the beverage material from sticking to the sides of the infusion chamber. Moreover, the introduction of air releases aroma which can optionally be vented via a conduit to a vent located in the vicinity of the spout, thereby providing the user with the aroma of tea during brewing. In a preferred embodiment, the aroma passes from the infusion chamber through a conduit to an aroma vent located in the vicinity of, and preferably adjacent to the spout 63. The brewing time, which typically ranges from 10 to 120 seconds, is preferably set by user input and/or information read from the capsule.

Once brewing has taken place for the required time the drain valve 21 is opened, allowing the beverage to drain from the infusion chamber. Preferably the opening of the drain valve is controlled automatically by the machine. The beverage flows from the infusion chamber through the filter 25. Infusible beverage material is prevented from entering the passage by the filter. The beverage then flows through the passage 29, out through the orifice(s) 40, into the vessel 60 and finally pours through the spout 63 into a cup 9 which the user has already placed onto the tray 8. Thus, rather than being dispensed vertically downwards into the cup, the beverage follows an arc, similar to that of tea poured from the spout of a tea pot. This emphasizes the "tea-ness" of the beverage, as distinct from coffee making machines. In the embodiment shown in FIG. 1, there is no direct connection between the vessel and the orifice. Thus the beverage is dispensed from the orifice and falls through free space, onto the vessel and out via the spout so that the consumer sees the tea pouring in an arc into the cup. Finally, after the beverage has been dispensed, the user removes the used capsule and spent tea leaves. The free space beneath the capsule holder makes it easy to remove the capsule holder after brewing, so that the used capsule can be disposed of. Similarly this space facilitates insertion of the capsule holder with a new capsule before brewing. In contrast, if the bottom of the capsule holder were in close proximity to the vessel, it would be less straightforward to remove and insert the capsule holder.

The various features of the embodiments of the present invention referred to in individual sections above apply, as appropriate, to other sections mutatis mutandis. Consequently features specified in one section may be combined with features specified in other sections as appropriate. Various modifications of the described modes for carrying out the invention which are apparent to those skilled in the relevant fields are intended to be within the scope of the following claims.

The invention claimed is:

1. A method of preparing a tea beverage in a capsule-based brewing device the device comprising:
   an infusion chamber comprising a first bottom surface;
   a capsule holder comprising:
      a top surface in water-tight contact with the first bottom surface; and
      a second bottom surface opposite the top surface, the capsule holder sized and shaped so as to receive a capsule, the capsule not comprising a filter therein;
   a filter;
   an openable and closable passage positioned along the second bottom surface and which terminates in an orifice;
   a cup or tray located beneath the orifice; and
   having a spout;
   the method comprising the steps of:
      a) brewing the beverage by releasing liquid and releasing infusible tea plant beverage material from the capsule into the infusion chamber; and
      b) after brewing has taken place for a sufficient time,
         (i) opening the passage to allow the beverage to flow from the infusion chamber through the filter, along the passage, through the orifice, and
         (ii) wherein the beverage is dispensed from the orifice and fails through free space into the cup or tray and out from the spout.

2. The method according to claim 1, wherein the devices further comprises an air pump in fluid communication with the infusion chamber; and
   wherein the method further comprises pumping air into the infusion chamber.

3. A capsule-based brewing device comprising:
   an infusion chamber comprising a first bottom surface;
   a capsule holder comprising:
      a top surface in water-tight contact with the first bottom surface; and
      a second bottom surface opposite the top surface, the capsule holder sized and shaped so as to receive a capsule, the capsule not comprising a filter therein;
   a filter;
   an openable and closable passage positioned along the second bottom surface and which terminates in an orifice;
   a cup or tray located beneath the orifice having a spout;
   wherein the cup or tray is not integral with the device;
   means for releasing liquid and infusible tea plant beverage material from the capsule into the infusion chamber so as to brew the beverage;
   wherein the liquid is water at a temperature of about 80° C. to about 95° C.;
   a valve for opening the passage to allow the beverage to flow from the infusion chamber through the filter, along the passage, through the orifice;
   wherein the beverage is dispensed from the orifice and falls through free space into the cup or tray and out from the spout.

4. The device according to claim 3, further comprising:
   an air pump in fluid communication with the infusion chamber.

* * * * *